(12) United States Patent
Tsubouchi et al.

(10) Patent No.: US 7,048,681 B2
(45) Date of Patent: May 23, 2006

(54) METHOD AND APPARATUS FOR ADJUSTING A LENGTH OF THE INFLOW CONDUIT ON A VENTRICULAR ASSIST DEVICE

(75) Inventors: Takeshi Tsubouchi, Ann Arbor, MI (US); Chisato Nojiri, Ann Arbor, MI (US)

(73) Assignee: Terumo Corporation, Tokyo (JP)

( * ) Notice: Subject to any disclaimer, the term of this patent is extended or adjusted under 35 U.S.C. 154(b) by 204 days.

(21) Appl. No.: 10/400,665

(22) Filed: Mar. 28, 2003

(65) Prior Publication Data

US 2004/0193004 A1    Sep. 30, 2004

(51) Int. Cl.
*A61N 1/362* (2006.01)
(52) U.S. Cl. ..................................................... 600/16
(58) Field of Classification Search ............ 600/16–18; 604/77, 79; 623/3.1, 3.26; 285/13, 18; 606/108; 137/426; 229/125.22, 566
See application file for complete search history.

(56) References Cited

U.S. PATENT DOCUMENTS

| | | | | |
|---|---|---|---|---|
| 2,771,237 A | * | 11/1956 | Philipson | ............... 229/125.22 |
| 4,182,364 A | * | 1/1980 | Gilbert et al. | ............... 137/426 |
| 4,216,980 A | * | 8/1980 | Shreve | .......................... 285/13 |
| 4,906,234 A | * | 3/1990 | Voychehovski | ............... 604/79 |
| 5,676,671 A | * | 10/1997 | Inoue | ........................... 606/108 |
| 6,001,056 A | | 12/1999 | Jassawalla et al. | |
| 6,050,975 A | | 4/2000 | Poirier | |
| 6,146,325 A | | 11/2000 | Lewis et al. | |
| 6,732,501 B1 | * | 5/2004 | Yu et al. | ........................ 600/16 |
| 6,892,969 B1 | * | 5/2005 | Dolan et al. | ................. 239/566 |
| 2002/0045846 A1 | | 4/2002 | Kaplon et al. | |
| 2002/0188167 A1 | | 12/2002 | Viole et al. | |

FOREIGN PATENT DOCUMENTS

| | | |
|---|---|---|
| FR | 2 788 223 A1 | 7/2000 |
| WO | WO 01/05447 A1 | 1/2001 |
| WO | WO 02/22200 A1 | 3/2002 |

* cited by examiner

*Primary Examiner*—George Manuel
(74) *Attorney, Agent, or Firm*—Buchanan Ingersoll PC (57) ABSTRACT

An inflow conduit system including an inflow conduit having a distal end, a proximal end, and a body portion extending therebetween, and an apical cuff assembly having a sleeve portion and a ring portion. When in use, the apical cuff assembly is disposed over the inflow conduit such that a predetermined tip length of the body portion is defined between the distal end of the inflow conduit and the ring portion, the predetermined tip length being determinable based upon a position of the sleeve portion relative to the inflow conduit.

21 Claims, 7 Drawing Sheets

METHOD AND APPARATUS FOR ADJUSTING A LENGTH OF THE INFLOW CONDUIT ON A VENTRICULAR ASSIST DEVICE

TECHNICAL FIELD

The present invention relates to a ventricular assist device (VAD), and more particularly to a system for adjusting the length of the inflow conduit on a VAD and a method of using the same.

BACKGROUND OF THE INVENTION

With recent medical developments, the human life expectancy is becoming longer, however, the ratio of cardiac failure to all the various causes of death is also increasing. Ventricular assist devices have become increasingly recognized as potentially able to allow patient's whose natural heart is diseased or has been injured by trauma or heart attack, to recover and continue life, either while their natural heart heals, while awaiting a heart transplant, or even on a long-term basis.

In particular, left-ventricular assist devices (LVAD) are recognized as potentially very valuable for assisting patients who suffer from congestive heart failure. The LVAD was developed for the treatment of end stage congestive heart failure in patients who are on maximal medical therapy and require long-term mechanical circulatory support, for example, patients who are not (temporarily or permanently) candidates for heart transplantation.

A LVAD is able to assume the function of the left ventricle, and thus continue perfusion of oxygen-rich blood into the body. The LVAD attaches to the patient's natural heart, and to a natural artery, and can be removed if the natural heart recovers. Some LVADs are surgically implanted into the patient's abdominal cavity, while others remain outside the body and are placed in fluid communication with the heart via elongated cannulas. Blood flow in the LVAD is effected by expansion and contraction of a variable-volume chamber. One-way valves associated with the inflow and outflow ports of the LVAD provide for blood flow into the variable-volume chamber during expansion, and for blood flow out of this chamber, usually to the ascending thoracic aorta. A pair of conduits respectively connect the inlet port of the assist device to the left ventricle and the outlet port to the major artery which is to receive the blood flow from the device. A typical LVAD is shown and described in U.S. Pat. No. 6,001,056, the entire contents of which are hereby incorporated by reference.

Alternatively, a VAD can be applied to replace or augment the function of the right ventricle (RVAD). As such, for the purposes of the present invention, the use of VAD applies to both LVADs and RVADs.

Figure 1:
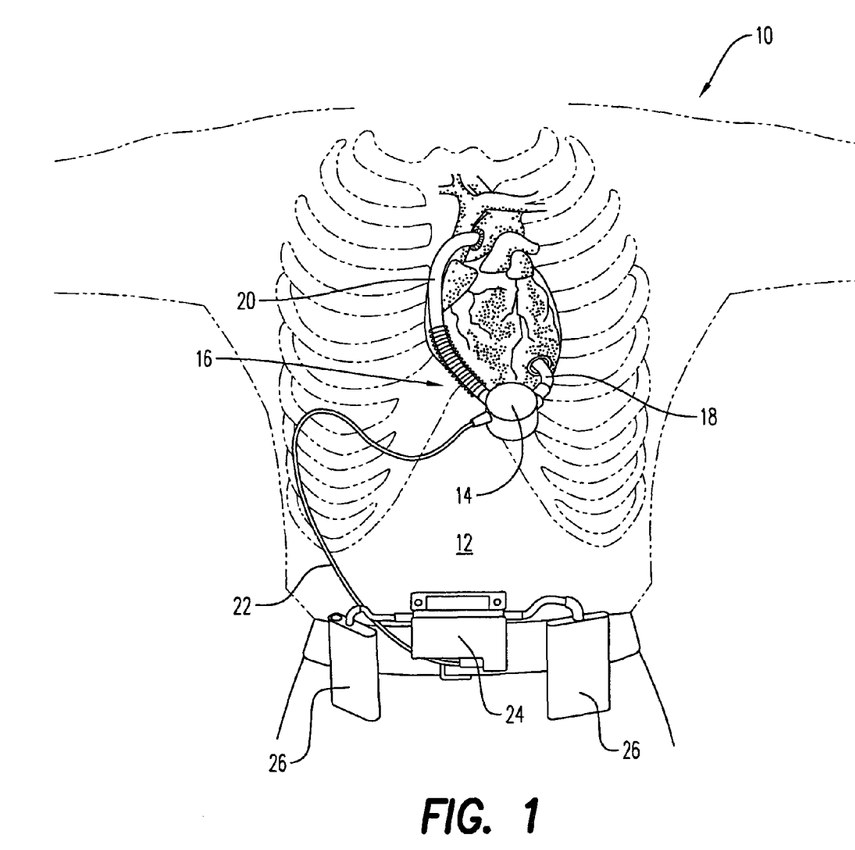
FIG. 1 is a front view of an exemplary left ventricular assist device illustrated connected to a heart of a patient.

With reference to FIG. 1, a patient 10 is shown in fragmentary front elevational view. Surgically implanted into the patient's abdominal cavity 12 is the pumping portion 14 of a ventricular assist device, generally referenced with the numeral 16. The ventricular assist device 16 includes an inflow conduit 18 conveying blood from the patient's left ventricle into the pumping portion 14, and an outflow conduit 20 conveying blood from the pumping portion 14 to the patients ascending thoracic aorta. From the pumping portion 14, a power cable 22 extends outwardly of the patient's body via an incision to a compact controller 24. A power source, such as a battery pack worn on a belt about the patient's waist, and generally referenced with the numeral 26, is connected with the controller 24.

Each of the conduits 18, 20 includes a tubular metallic housing proximate the pumping portion 14 of the device which may connect to elongated flexible segments extending to the heart and ascending aorta, respectively. At the end of the inflow conduit 18 which is connected to the patient's heart, and at the end of the outflow conduit 20 which is connected to the ascending thoracic aorta, the conduits are generally attached to the natural tissue by sutures through the use of an apical sewing ring so that blood flow communication is established and maintained.

The distal end of the inflow conduit 18 is inserted through the ventricle wall and into the heart in order to establish blood flow from the heart to the pumping portion 14. The length of the inflow conduit which passes through the ventricle wall and into the heart is important in order to avoid blood clotting while still ensuring adequate blood flow. If for example, the length of inflow conduit which is inserted into the heart is too great, the tip of the inflow conduit will touch the opposing wall or the septum wall of the heart and thereby suction tissue into the conduit. On the other hand, if the length of the inflow conduit is too short, tissue and muscle ingrowth around the conduit tip opening will eventually create an occlusion, thereby blocking the conduit and preventing an adequate blood flow. Obtaining the appropriate length of inflow conduit is difficult to achieve, however, because while the inflow conduit is generally a fixed length, the thickness of the ventricular wall varies depending upon the patient.

Accordingly, there exists a need for a reliable and efficient system for adjusting the length of the inflow conduit which extends interior to the ventricular wall of the heart during implantation of a VAD.

SUMMARY OF THE INVENTION

The present invention provides an inflow conduit system including an inflow conduit comprising a distal end, a proximal end, and a body portion extending therebetween. The system further includes an apical cuff assembly comprising a sleeve portion and a ring portion. Accordingly, when in use, the apical cuff assembly is disposed over the inflow conduit such that a predetermined tip length of the body portion is defined between the distal end of the inflow conduit and the ring portion. The predetermined tip length is determinable based upon a position of the sleeve portion relative to the inflow conduit. In a preferred embodiment, the body portion includes a plurality of indicators, and more preferably, the plurality of indicators includes a plurality of lines formed on the body portion at predetermined intervals. Most preferably, at least some of the plurality of lines are numbered to represent a unit of measurement.

The present invention further provides a method for adjusting the tip length of an inflow conduit when inserted into the heart of a patient. The method comprises positioning an apical cuff assembly over the inflow conduit to a desired position such that a predetermined tip length of the inflow conduit extends interior to the heart wall of the patient, and determining the predetermined tip length based upon the position of the apical cuff assembly relative to the inflow conduit, wherein the predetermined tip length is adjustable by repositioning the apical cuff assembly relative to the inflow conduit. In a preferred embodiment the apical cuff assembly includes a sleeve portion and a ring portion and the determining step further comprises determining the predetermined tip length based upon the position of the sleeve portion relative to the inflow conduit. More preferably, the inflow conduit includes a plurality of indicators and the determining step further comprises determining the predetermined tip length based upon the position of the sleeve portion relative to the plurality of indicators. The preferred embodiment further comprises suturing the ring portion of the apical cuff assembly to heart tissue of the patient.

BRIEF DESCRIPTION OF THE DRAWINGS

For further understanding of the nature and objects of the present invention, references made to the following detailed description taken in conjunction with the accompanying drawings in which like parts are given like reference numerals, wherein.

DETAILED DESCRIPTION OF THE INVENTION

Figure 2:
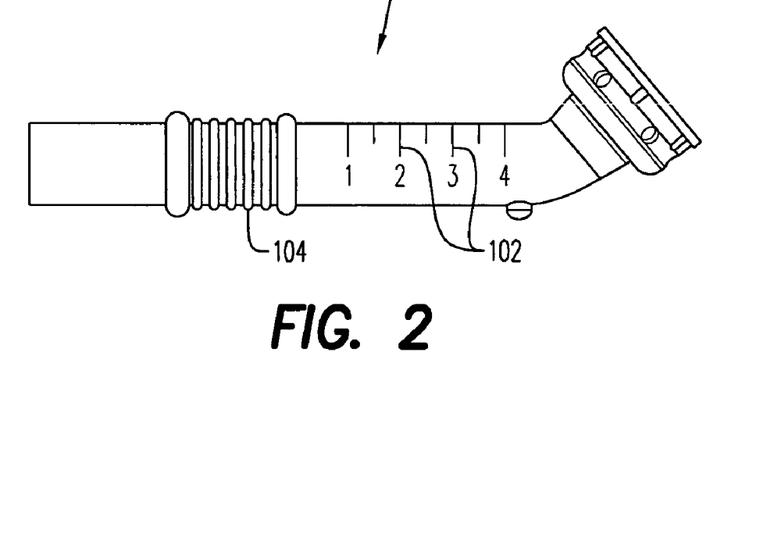
FIG. 2 is an inflow conduit according to the present invention.
Figure 3:
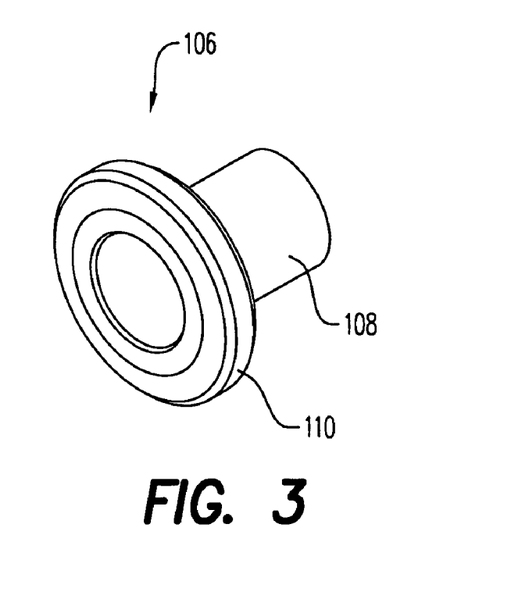
FIG. 3 is a perspective view of an apical cuff assembly according to the present invention.
Figure 4:
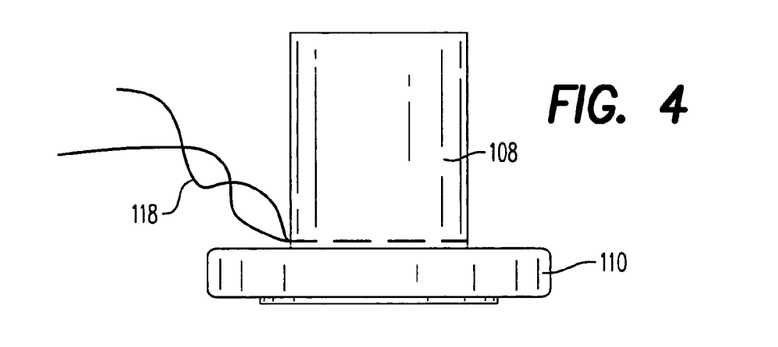
FIG. 4 is an elevational view of the apical cuff assembly.
Figure 5:
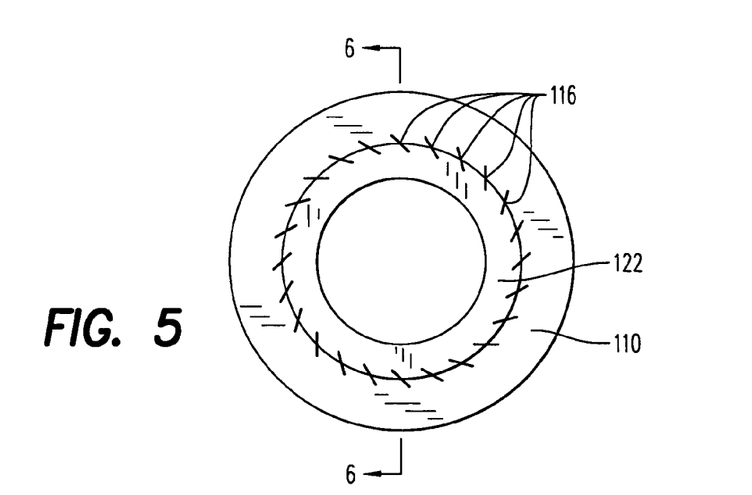
FIG. 5 is a front view of the apical cuff assembly.
Figure 6:
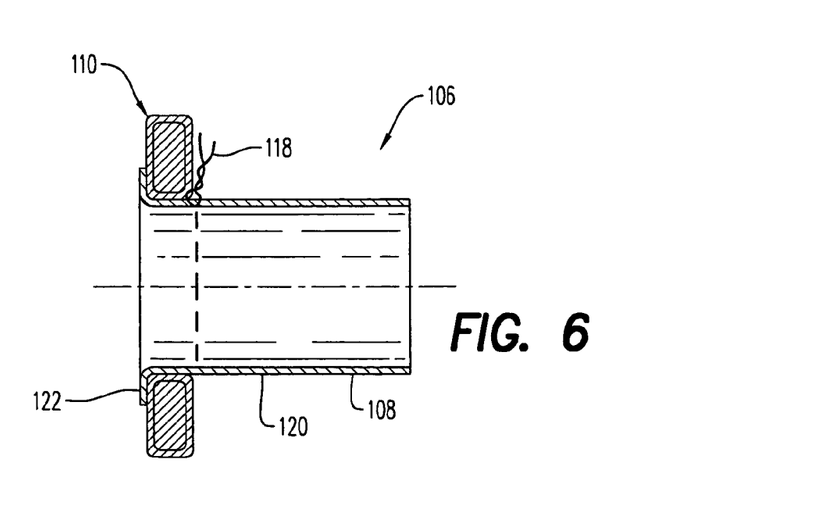
FIG. 6 is a cross-sectional view through the apical cuff assembly.

Referring to FIG. 2, the present invention includes an inflow conduit 100 for insertion into the ventricle, most preferably the left ventricle, of a patient. The inflow conduit 100 is preferably marked with a plurality of indicators 102, such as the indicator lines denoted by 1, 2, 3, etc. in the illustrated embodiment, which are scored or etched into the conduit at predetermined intervals, such as centimeters, millimeters, etc. The purpose of the indicators is explained below. In a preferred embodiment, the conduit 100 is made of titanium, has a diameter of approximately 14 mm and a length of approximately 88 mm. Other materials, diameters and lengths could of course also be used without departing from the scope of the present invention. For instance, plastic materials such as ultra high molecular polyethylene could also be used.

The inflow conduit 100 also includes at least one locking mechanism 104 preferably defined by at least one protrusion on the outer surface of the conduit having a diameter slightly greater than that of the inflow conduit. In a preferred embodiment, the locking mechanism 104 includes a plurality of protrusions having a maximum diameter of approximately 1 mm to 3 mm greater than the diameter of the inflow conduit 100. As explained below in greater detail, the locking mechanism 104, in combination with one or more laces or threads, assists in preventing the apical cuff assembly of the present invention from pulling off of the inflow conduit 100 after implantation into the patient.

With reference also to FIGS. 3–6, an apical cuff assembly 106 according to the present invention is illustrated. The apical cuff assembly includes a ring member 110 and an apical cuff sleeve graft 108 which are joined together preferably by stitching 116, although other known methods of attachment could also be used. The apical cuff assembly 106 also preferably includes one or more laces 118 embedded about the sleeve graft 108 which may be tightened and then tied in order to maintain the apical cuff assembly 106 in the desired position on the inflow conduit 100, as explained in greater detail below.

Figure 7:
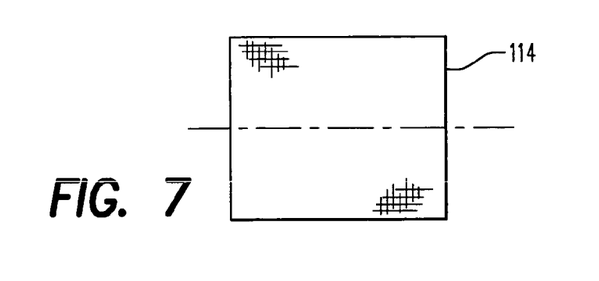
FIG. 7 is an elevational view of the ring wrap cloth.
Figure 8:
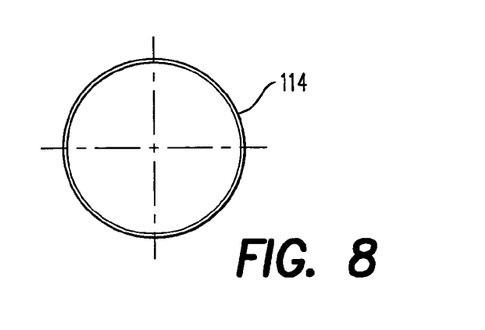
FIG. 8 is an end view thereof.
Figure 9:
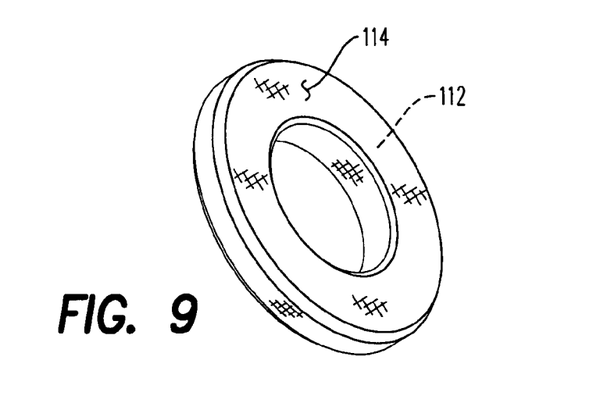
FIG. 9 is a perspective view thereof when wrapped around the apical cuff inner ring.
Figure 13:
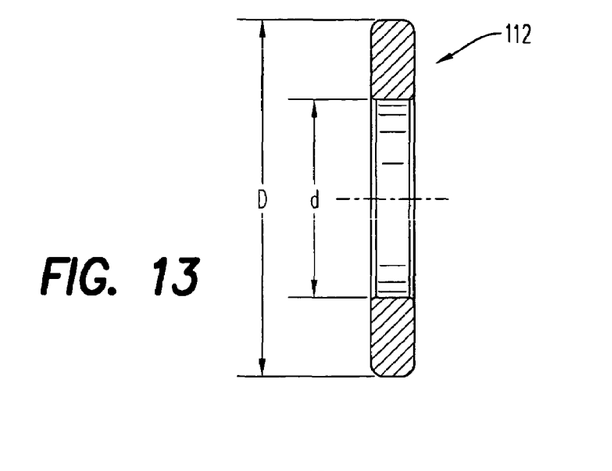
FIG. 13 is a cross sectional view of the apical cuff inner ring.
Figure 14:
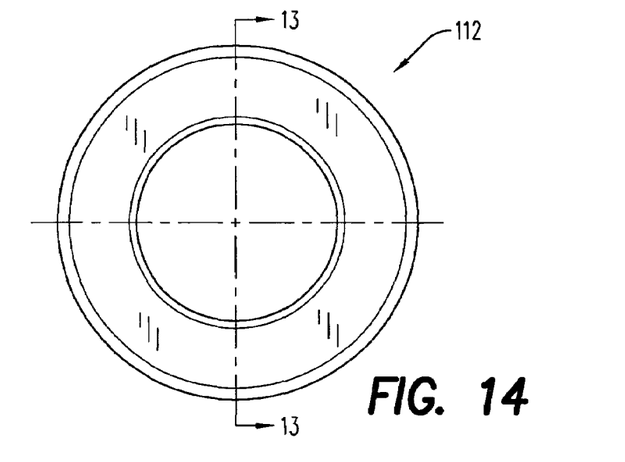
FIG. 14 is an end elevational view thereof.
Figure 15:
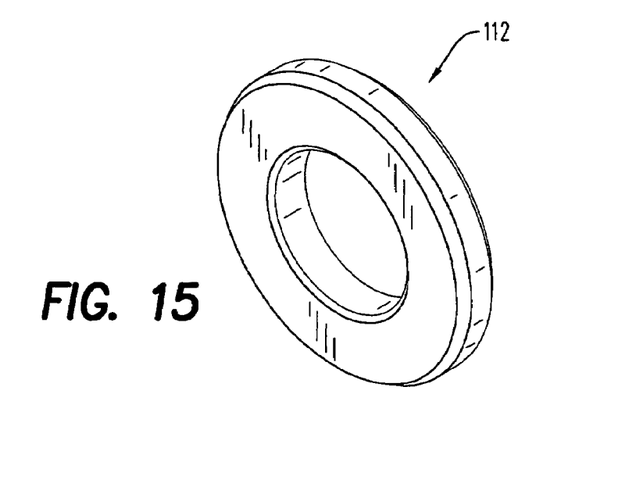
FIG. 15 is a perspective view thereof.

The ring member 110 is comprised of an inner ring 112 that is covered by a cloth wrap 114. Referring to FIGS. 13–15, the inner ring 112 is preferably made from silicone rubber. In a preferred embodiment, the outer diameter "D" of the inner ring 112 is approximately 32 mm and the inner diameter "d" is approximately 18 mm. The thickness of the inner ring 112 is approximately 3.7 mm in a preferred embodiment. Referring to FIGS. 7–9, the cloth wrap 114 is preferably made of polyester, and most preferably a woven polyester. As shown in FIG. 9, the cloth wrap 114 preferably extends entirely around the inner ring 112 and the opposing edges are sewn or otherwise joined together. The ring member 110 is preferably sutured into place on the heart tissue with sutures 124 (FIG. 17) and must therefore be durable enough to withstand the suturing process. The silicone rubber from which the inner ring 112 is preferably made may tear if it were sutured directly to the heart. Accordingly, the cloth wrap 114 strengthens the ring member 110 by using a material suitable for suturing to natural tissue.

Figure 10:
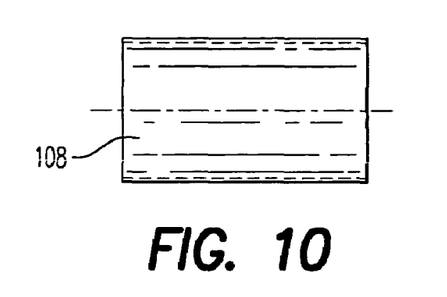
FIG. 10 is an elevational view of the apical cuff sleeve graft.
Figure 11:
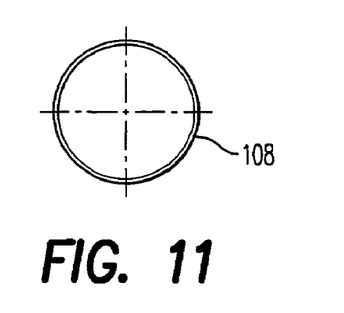
FIG. 11 is an end view thereof.
Figure 12:
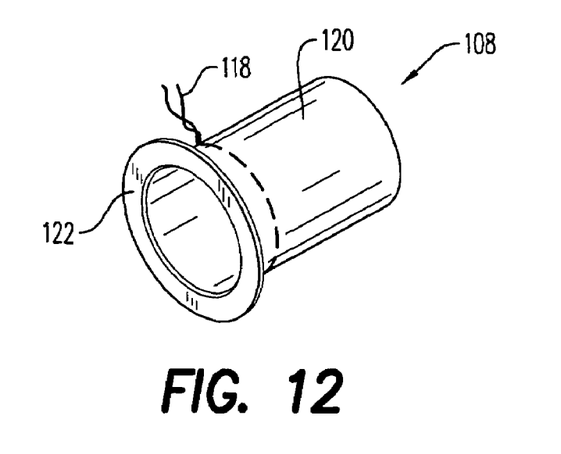
FIG. 12 is a perspective view thereof.

The apical cuff sleeve graft 108 shown in FIGS. 10–12 is preferably comprised of polyester, and most preferably a knitted polyester. The sleeve graft 108 includes a cylindrical body portion 120 including one or more laces 118 extending therearound, and a flared edge portion 122. As shown most clearly in FIGS. 5 and 6, the sleeve graft 108 is inserted through the opening of the ring member 110 such that the distal surface of the ring member 110 engages the proximal surface of the flared edge portion 122. The surfaces are then attached by stitching 116 or other attachment means.

Figure 16:
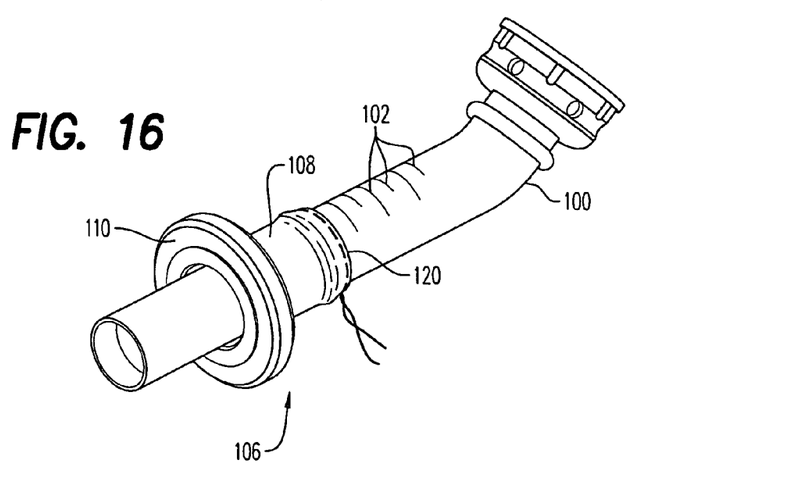
FIG. 16 is a perspective view of the apical cuff assembly inserted onto the inflow conduit.
Figure 17:
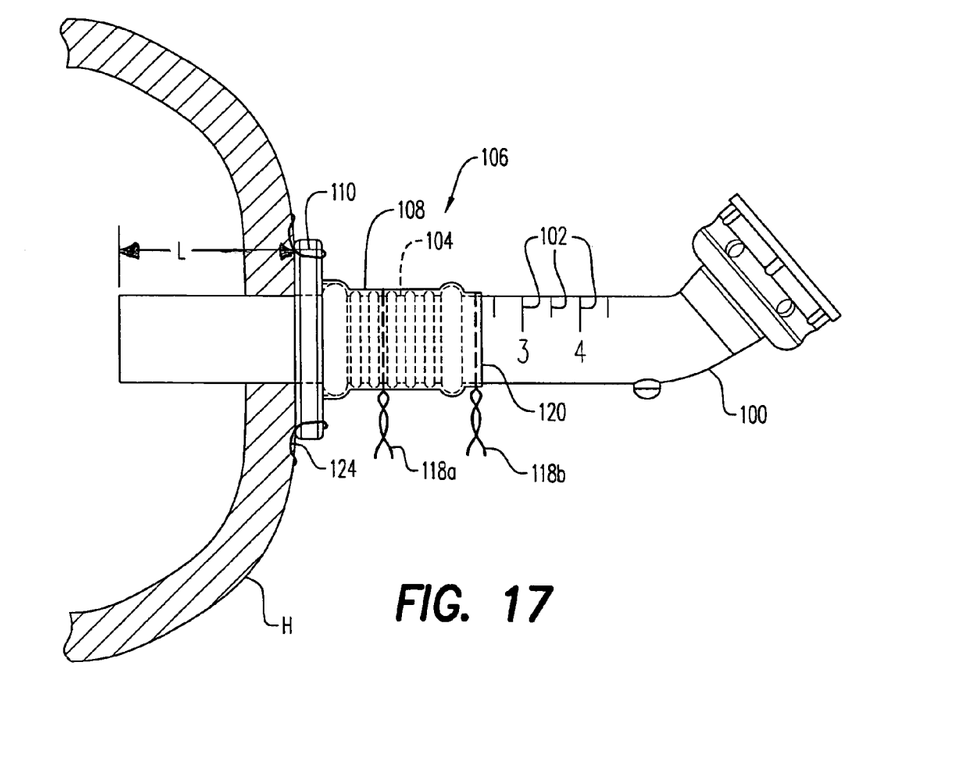
FIG. 17 is a side elevational view thereof illustrating the position when in use in a patient.

Referring to FIGS. 16 and 17, the apical cuff assembly 106 is disposed over the inflow conduit 100 until the terminal end 120 of the apical cuff sleeve graft 108 is properly aligned with or between the desired indicator 102, as determined by the surgeon based upon the thickness of the patient's heart wall. More specifically, the indicators 102, as numbered 1, 2, 3, 4 in the illustrated embodiment correspond to measurement units, preferably centimeters, for the tip length "L" of inflow conduit 100 which extends distal to the ring member 110 and interior to the heart wall when the assembly 106 is disposed thereover. Accordingly when the inflow conduit 100 is inserted through the ventricular wall, the ring member 110 will come to rest on the exterior of the ventricular wall of the heart "H" and only the tip length "L" of the inflow conduit will extend distally from the ring member, through the heart wall and interior to the heart. In this manner, by adjusting the position of the apical cuff assembly 106 on the inflow conduit 100, the length of conduit between the distal end of the inflow conduit and the ring portion and thus the tip length of the inflow conduit protruding into the heart chamber can be accurately and easily adjusted.

The laces 118a and 118b are tied to securely fasten the apical cuff assembly 106 on the inflow conduit 100. As shown in the illustrated embodiment, at least one of the laces 118 is disposed proximal to the locking mechanism 104. Thus, when internal forces, such as those produced by the beating heart, body movement or breathing, cause the sutured ring member 110 to pull the apical cuff assembly 106 in a distal direction (toward the heart), distal movement of the apical cuff assembly is halted by the lace 118 engaging the locking mechanism 104. To further secure the connection of the apical cuff assembly 106 to the inflow conduit 100, the cuff and conduit may be covered with a flexible wrap material or tape, such as PTFE tape.

While the present invention has been depicted, described, and is defined by reference to a particularly preferred embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiment of the invention is exemplary only, and is not exhaustive of the scope of the invention. Consequently, the invention is intended to be limited only by the spirit and scope of the appended claims, giving full cognizance to equivalents in all respects.

What is claimed is:

1. An inflow conduit system comprising:
   an inflow conduit comprising a distal end for insertion into the heart of a patient, a proximal end, and a body portion extending therebetween;
   an apical cuff assembly comprising a cylindrical sleeve portion and a ring portion extending radially outwardly from a terminal end of the sleeve portion;
   wherein when in use said apical cuff assembly is disposed over said inflow conduit such that said ring portion abuts an exterior surface of a heart wall, said distal end of the inflow conduit extends interior to the heart wall, and a predetermined tip length of said body portion is defined between said distal end and said ring portion, said predetermined tip length being determinable based upon a position of said sleeve portion relative to said proximal end of said inflow conduit.

2. The inflow conduit system of claim 1, wherein said body portion includes a plurality of indicators and said predetermined tip length is determinable based upon the position of said sleeve portion relative to said plurality of indicators.

3. The inflow conduit system of claim 2, wherein said plurality of indicators include a plurality of lines formed on said body portion at predetermined intervals.

4. The inflow conduit system of claim 3, wherein at least some of said plurality of lines are numbered to represent a unit of measurement.

5. The inflow conduit system of claim 3, wherein said plurality of lines are scored or etched into said body portion.

6. The inflow conduit system of claim 1, wherein said body portion is formed of titanium.

7. The inflow conduit system of claim 1, wherein said sleeve portion has a first end and a second end, said ring portion being connected to said sleeve portion at one of said first and second ends.

8. The inflow conduit system of claim 7, wherein said first end comprises a flange portion and said ring portion is connected to said flange portion.

9. The inflow conduit system of claim 8, wherein said flange portion and said ring portion are connected by stitching.

10. The inflow conduit system of claim 8, wherein a proximal surface of said flange portion engages a distal surface of said ring portion.

11. The inflow conduit system of claim 7, wherein said ring portion includes an inner ring and a surrounding cloth wrap.

12. The inflow conduit system of claim 11, wherein said inner ring is formed from silicone rubber.

13. The inflow conduit system of claim 12, wherein said cloth wrap is polyester.

14. The inflow conduit system of claim 7, wherein said sleeve portion is polyester.

15. The inflow conduit system of claim 7, wherein said sleeve portion includes at least one lace extending circumferentially therearound.

16. The inflow conduit system of claim 15, wherein said body portion includes at least one locking mechanism such that when said at least one lace is drawn tight around said inflow conduit, translational movement of said apical cuff assembly is substantially prevented by said at least one locking mechanism.

17. The inflow conduit system of claim 16, wherein said at least one locking mechanism comprises a protuberance defining a diameter greater than a diameter of said inflow conduit.

18. A method for adjusting the tip length of an inflow conduit when inserted into the heart of a patient, said method comprising:
   positioning an apical cuff assembly over the inflow conduit to a desired position such that a predetermined tip length of the inflow conduit extends interior to the heart wall of the patient;
   verifying insertion of the predetermined tip length based upon the position of the apical cuff assembly relative to the inflow conduit;
   wherein the predetermined tip length is adjustable by repositioning the apical cuff assembly relative to the inflow conduit.

19. The method of claim 18, wherein the apical cuff assembly includes a sleeve portion and a ring portion and said determining step further comprises determining the predetermined tip length based upon the position of the sleeve portion relative to the inflow conduit.

20. The method of claim 19, wherein the inflow conduit includes a plurality of indicators and said determining step further comprises determining the predetermined tip length based upon the position of the sleeve portion relative to the plurality of indicators.

21. The method of claim 19, further comprising suturing the ring portion of the apical cuff assembly to heart tissue of the patient.

* * * * *